(12) United States Patent
Parikh et al.

(10) Patent No.: US 9,511,145 B2
(45) Date of Patent: Dec. 6, 2016

(54) STABLE TIGECYCLINE COMPOSITION

(71) Applicant: Intas Pharmaceuticals Limited, Ahmedabad, Gujarat (IN)

(72) Inventors: Dhara Parikh, Ahmedabad (IN); Aditya Patel, Ahmedabad (IN); Pallerla Bhaskar, Ahmedabad (IN); Ashish Sehgal, Ahmedabad (IN)

(73) Assignee: Intas Pharmaceuticals Limited, Ahmedabad (IN)

( * ) Notice: Subject to any disclaimer, the term of this patent is extended or adjusted under 35 U.S.C. 154(b) by 0 days.

(21) Appl. No.: 14/779,889

(22) PCT Filed: Mar. 25, 2014

(86) PCT No.: PCT/IN2014/000186
§ 371 (c)(1),
(2) Date: Sep. 24, 2015

(87) PCT Pub. No.: WO2014/167575
PCT Pub. Date: Oct. 16, 2014

(65) Prior Publication Data
US 2016/0058865 A1  Mar. 3, 2016

(30) Foreign Application Priority Data

Mar. 26, 2013 (IN) .................. 1127/MUM/2013

(51) Int. Cl.
*A61K 47/26* (2006.01)
*A61K 31/65* (2006.01)

(52) U.S. Cl.
CPC ............... *A61K 47/26* (2013.01); *A61K 31/65* (2013.01)

(58) Field of Classification Search
None
See application file for complete search history.

(56) References Cited

U.S. PATENT DOCUMENTS

| | | |
|---|---|---|
| RE40,183 E | 3/2008 | Hlavka et al. |
| 7,705,168 B2 | 4/2010 | Chanana et al. |
| 7,879,828 B2 | 2/2011 | Fawzi et al. |
| 2009/0275660 A1 | 11/2009 | Chauhan et al. |
| 2010/0035845 A1 | 2/2010 | Ofslager et al. |
| 2010/0197650 A1 | 8/2010 | Biek |

FOREIGN PATENT DOCUMENTS

WO   2006/099258   9/2006

OTHER PUBLICATIONS

Database CAPLUS in STN, Acc. No. 2010:1609957, Lu et al., CN 101919816 A (Dec. 22, 2010) (abstract).*
Database CAPLUS in STN, Acc. No. 2009:345703, Shao et al., CN 101386582 A (Mar. 18, 2009) (abstract).*
International Search Report issued in International Application No. PCT/IN2014/000186, Sep. 26, 2014, 3 pages.

* cited by examiner

*Primary Examiner* — Brian J Davis
(74) *Attorney, Agent, or Firm* — Hamre, Schumann, Mueller & Larson, P.C.

(57) ABSTRACT

The present invention relates to a stable pharmaceutical composition of Tigecycline and process for the preparation of the same. The composition comprises Tigecycline and maltose wherein the pH of the bulk solution or solution after reconstitution is in between 3-6.

6 Claims, No Drawings

STABLE TIGECYCLINE COMPOSITION

FILED OF THE INVENTION

The present invention relates to a stable pharmaceutical composition comprising Tigecycline and maltose. Further the present invention discloses process for the preparation of the said composition.

BACKGROUND OF THE INVENTION

Tigecycline is a tetracycline derivative (a glycylcycline) which is a chemically (4S,4aS,5aR,12aS)-9-[2-(tert-butylamino)acetamido]-4,7bis(dimethylamino)-1,4,4a,5,5a,6,11,12a-octahydro-3,10,12,12a-tetrahydroxy-1,11-dioxo-2-naphthacenecarboxamide. Molecular formula of Tigecycline is $C_{29}H_{39}N_5O_8$ and the molecular weight is 585.65 and has following chemical structure:

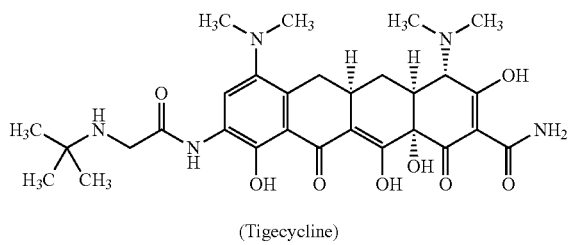 [SMILES: CN(C)c1cc(NC(=O)CNC(C)(C)C)c(O)c2c1C[C@H]1C[C@H]3[C@H](N(C)C)C(O)=C(C(N)=O)C(=O)[C@@]3(O)C(O)=C1C2=O]

(Tigecycline)

USRE40183 discloses 7-substituted-9-substituted amino-6-demethyl-6-deoxytetracyclines which cover Tigecycline. Tigecycline is marketed as lyophilized powder for reconstitution for intravenous infusion under trade name TYGACIL® by Wyeth; which contains Tigecycline as active ingredient and lactose monohydrate as inactive ingredient. Tigecycline is approved for complicated skin and skin structure infections, complicated intra-abdominal infections and community-acquired bacterial pneumonia.

From literature it is known that Tigecycline undergoes degradation by two different pathways. One of them is oxidative degradation and another one is epimerization. Oxidative degradation can be controlled by lowering pH of the composition. At lower pH, epimerization emerges as the most predominant degradation pathway. To overcome the said problem several approaches are reported as follows:

Tigecycline is currently marked as TYGACIL® by Wyeth; which contains lactose monohydrate as inactive ingredient. The pH of the composition after reconstitution is acidic. The composition uses lactose monohydrate as stabilizer to control the degradation of Tigecycline by epimerization pathways.

U.S. Pat. No. 7,879,828 discloses a composition comprising tigecycline, lactose, and an acid selected from hydrochloric acid and gentisic acid, and the pH of the composition in a solution is between about 3.0 and about 7.0. Focus of U.S. Pat. No. 7,879,828 is to use lactose and lower pH to get stable composition of Tigecycline.

U.S. Pat. No. 7,705,168 discloses a manufacturing process for the production of tigecycline as a reconstitutable powder having less than 0.9% total degradants comprising the steps of reducing and maintaining the oxygen level in water for injection to less than or equal to 0.5 ppm. Focus of U.S. Pat. No. 7,705,168 is to control oxidation pathway by controlling oxygen level.

US2009275660 discloses stable parenteral formulations of tigecycline and process of preparation thereof, wherein the formulation comprises of an edetate, a pH modifying agent or an antioxidant, such that the formulation remains stable for at least 45 hours. Focus of US2009275660 is to provide stable composition by using edetate.

US2010035845 discloses a frozen pharmaceutical formulation suitable for administration to a subject parenterally, comprising a therapeutically effective amount of tigecycline and an agent selected from the group consisting of lactose, dextrose, glucose, mannose, sucrose, ribose, xylose and a combination thereof.

Focus of US2010035845 is to use lactose, dextrose, glucose, mannose, sucrose, ribose, xylose to get stable composition of Tigecycline.

Considering the prior efforts as disclosed in the background, a need exists which would addresses the issues relating to degradation of Tigecycline in the pharmaceutical composition and provides a stable pharmaceutical composition of Tigecycline.

OBJECT OF THE INVENTION

The present invention relates to a stable pharmaceutical composition comprising Tigecycline and maltose.

Another object of the present invention is to provide process for the preparation of a stable pharmaceutical composition comprising Tigecycline and maltose.

Another object of the present invention is to provide a stable pharmaceutical composition comprising Tigecycline and maltose wherein the pH of the composition after reconstitution is in between 3-6 preferably between 4-5 and more preferably between 4.3-4.9.

Another object of the present invention is to provide a stable pharmaceutical composition comprising Tigecycline and maltose wherein the composition is prepared from bulk solution comprises Tigecycline from 15-50 mg/mL, maltose from 30-100 mg/mL and pH of the bulk solution is in between 3-6, preferably between 4-5 and more preferably between 4.3-4.9.

Another object of the present invention is to provide process for preparation of a stable pharmaceutical composition comprising Tigecycline and maltose wherein the pH of the composition after reconstitution is in between 3-6 preferably between 4-5 and more preferably between 4.3-4.9.

Another object of the present invention is to disclose use of maltose as stabilizing agent for preparation of stable Tigecycline composition.

SUMMARY OF THE INVENTION

Present invention provides a stable pharmaceutical composition comprising Tigecycline and maltose. Further the invention provides a use of maltose as stabilizing agent for preparation of stable Tigecycline composition. In another embodiment the present invention provides a process for preparation of stable pharmaceutical composition comprising Tigecycline and maltose. In one another embodiment the present invention also provides a stable pharmaceutical composition comprising Tigecycline and maltose wherein the pH of the composition after reconstitution is in between 3-6.

DETAILED DESCRIPTION OF THE INVENTION

Present invention provides a stable pharmaceutical composition comprising Tigecycline and maltose and a process for the preparation of the said composition.

Further, according to the present invention, the stable pharmaceutical composition comprises Tigecycline and maltose; wherein the composition is prepared from bulk solution comprises Tigecycline from 15-50 mg/mL, maltose from 30-100 mg/mL and pH of the hulk solution is in between 3-6.

According to the present invention, a stable pharmaceutical composition is defined as a lyophilized composition comprising Tigecycline and maltose; wherein impurity 4-epimer of Tigecycline, is less than 3% throughout shelf life.

According to the present invention, 4-epimer of Tigecycline is having following structure:

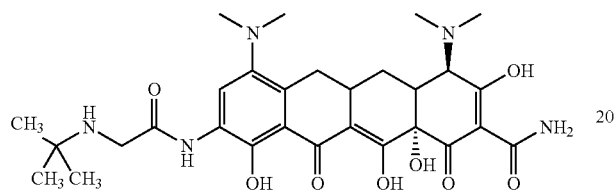

The stable pharmaceutical composition of the present invention is analyzed by HPLC method. The method of analysis by HPLC is well known in the art.

According to the present invention, a bulk solution is defined as a solution comprising Tigecycline and maltose, which is further lyophilized to obtain a stable pharmaceutical composition according to the present invention. The pH of the bulk solution is in between 3-6, wherein pH is attained by addition of pH adjusting agents like NaOH or HCl.

Lyophilization, also known as freeze drying, is a process in which solvent is removed from a bulk solution after it is frozen and placed under a vacuum, allowing the solvent to change directly from solid to gaseous phase without passing through a liquid phase. Lyophilization process is well known to the person skilled in the art.

According to present invention desired dissolved oxygen (DO) level refers to low amount of dissolved oxygen in solvent, preferably in the range of 0.5 ppm to 2 ppm.

In one of the embodiment, the present invention provides a process for the preparation of a stable pharmaceutical composition comprising Tigecycline and maltose comprising step of:
1. Taking WFI in manufacturing tank, sparging inert gas until desired dissolved oxygen level is attained.
2. Adding Maltose and Tigecycline to the solution of step 1 in any order and adjusting pH of the solution in between 3-6.
3. Optionally filtering the bulk solution through suitable filter.
4. Filling the required solution into vials, loading the vials into lyophilizer.
5. Running suitable lyophilization cycle to get the stable pharmaceutical composition comprising Tigecycline and maltose.

In one of the embodiment, a process for preparation of a stable pharmaceutical composition comprising step of adding maltose and Tigecycline to the water for injection (WFI) in any order and adjusting pH of the solution in between 3-6.

In one of the embodiment, a process for preparation of a stable pharmaceutical composition comprising a step of adding maltose and Tigecycline to the water for injection (WFI) in any order; wherein Hydrochloric acid is added prior to the addition Tigecycline.

In one of the embodiment, the present invention provides a process for the preparation of a stable pharmaceutical composition comprising Tigecycline and maltose comprising step of:
1. Taking WFI in manufacturing tank, sparging inert gas until desired dissolved oxygen level is attained.
2. Adding Maltose to the solution of step 1 and stir.
3. Adding Hydrochloric acid solution in solution of step 2 q.s. to pH approx. 1.1 and stir.
4. Adding Tigecycline to the solution of step 3 and stir.
5. Adjusting pH of the solution to approx 4.7.
6. Volume make up to batch size.
7. Optionally filtering the bulk solution through suitable filter.
8. Filling the required solution into vials, loading the vials into lyophilizer.
9. Running suitable lyophilization cycle to get the stable pharmaceutical composition comprising Tigecycline and maltose.

In one of the embodiment, the present invention provides a stable pharmaceutical composition comprising Tigecycline and maltose wherein the pH of the composition after reconstitution is in between 3-6 preferably between 4-5 and more preferably between 4.3-4.9 and process for preparation of the same.

In one of the embodiment, the present invention discloses use of maltose as stabilizing agent for preparation of stable Tigecycline composition.

EXAMPLES

The present invention has been described by way of example only, and it is to be recognized that modifications thereto filling within the scope and spirit of appended claims, and which would be obvious to a person skilled in the art based upon the disclosure herein, are also considered to be within the scope of this invention.

Example 1

Composition of Tigecycline Bulk Solution

| Sr. no. | Ingredients | Injection 50 mg/Vial Bulk Solution (mg/mL) |
|---|---|---|
| 1. | Tigecycline* | 25.00* |
| 2. | Maltose Monohydrate | 50.00 |
| 3. | Hydrochloric Acid | q.s. to pH |
| 4. | Sodium Hydroxide | q.s. to pH |
| 5. | Water for Injection** | q.s. to 1 mL** |

*Potency correction to be done
**Removed during lyophilization process
Note:
pH of the bulk/reconstituted solution is approx. 4.5.

Manufacturing Procedure

1. Taking WFI (2-8° C.) in manufacturing tank, sparging inert gas until desired dissolved oxygen level is attained.
2. Adding Maltose and Tigecycline to the solution of step 1 in any order.
3. Adjusting pH of the solution to approx. 4.5.
4. Optionally filtering the bulk solution through suitable filter.

5. Filling the required solution into vials, loading the vials into lyophilizer.
6. Running suitable lyophilization cycle to get the stable pharmaceutical composition comprising Tigecycline and maltose.

Example 2

Composition of Tigecycline Bulk Solution

| Sr. no. | Ingredients | Injection 50 mg/Vial Bulk Solution (mg/mL) |
|---|---|---|
| 1. | Tigecycline* | 35.00* |
| 2. | Maltose Monohydrate | 70.00 |
| 3. | Hydrochloric Acid | q.s. to pH |
| 4. | Sodium Hydroxide | q.s. to pH |
| 5. | Water for Injection** | q.s. to 1 mL** |

*Potency correction to be done
**Removed during lyophilization process
Note:
pH of the bulk/reconstituted solution is approx. 4.7.

Manufacturing Procedure

1. Taking WFI in manufacturing tank, sparging inert gas until desired dissolved oxygen level is attained.
2. Adding Maltose to the solution of step 1 and stir.
3. Adding Hydrochloric acid solution in solution of step 2 q.s. to pH approx. 1.1 and stir.
4. Adding Tigecycline to the solution of step 3 and stir.
5. Adjusting pH of the solution to approx 4.7.
6. Volume make up to batch size.
7. Optionally filtering the bulk solution through suitable filter.
8. Filling the required solution into vials, loading the vials into lyophilizer.
9. Running suitable lyophilization cycle to get the stable pharmaceutical composition comprising Tigecycline and maltose.

Lyophilized product obtained according to example 1 and 2 comprises of Tigecycline and maltose; wherein the pH of the composition after reconstitution is in between 3-6.

Stability study: The stability study of the composition obtained by example 2 was carried out at 25° C. and 60% RH, 40° C. and 75% RH and 50° C. for 1 month. The results obtained in the stability study are given below:

Stability Study Data

| Remark | Initial | 14 days/50° C. | 14 days/40° C. | 1 M/50° C. | 1 M/40° C. | 1 M/25° C. |
|---|---|---|---|---|---|---|
| Description | $ | $ | $ | $ | $ | $ |
| Assay | 105.7 | NA | NA | 105.4 | 106.7 | 106.7 |
| Related Substance | | | | | | |
| 9-amino Minocycline | 0.022 | 0.026 | 0.04 | 0.034 | 0.034 | 0.034 |
| 9-nitro minocycline | ND | ND | ND | ND | ND | ND |
| 4-epimer of tigecycline | 0.359 | 1.363 | 0.577 | 1.699 | 0.799 | 0.504 |
| Minocycline | ND | ND | ND | 0.02 | 0.019 | 0.013 |
| Any other individual impurity | 0.107 (RRT 0.75) | 0.126 (RRT 0.89), 0.118 (RRT 0.74) | 0.123 (RRT 0.74), 0.121 (RRT 0.89) | 0.098 (RRT 0.79), 0.011 (RRT 0.75), 0.064 (RRT 0.85) | 0.087 (RRT 0.79), 0.051 (RRT 0.85). | 0.083 (RRT 0.79) |
| Total impurity (other than 4-epimer) | 0.19 | 0.335 | 0.284 | 0.349 | 0.322 | 0.290 |
| Water | 2.81% | NA | NA | 3.49% | 2.38% | 3.50% |
| Reconstitution time | 40 seconds | NA | NA | 44 seconds | 41 seconds | 43 seconds |
| pH | 4.75 | NA | NA | 4.77 | 4.77 | 4.73 |

$ - Orange lyophilized cake in a clear glass vial

From the stability study data, it is concluded the composition comprising Tigecycline and maltose is found stable.

We claim:

1. A stable lyophilized pharmaceutical composition, comprising: Tigecycline and maltose, wherein the composition is prepared from a bulk solution that comprises the Tigecycline from 15-50 mg/mL and the maltose from 30-100 mg/mL.

2. The stable lyophilized pharmaceutical composition according to claim 1, wherein the pH of the bulk solution is between 3-6.

3. The stable lyophilized pharmaceutical composition according to claim 1, wherein after reconstitution, the pH of the stable lyophilized pharmaceutical composition is between 3-6.

4. A process for preparation of a stable lyophilized pharmaceutical composition according to claim 1, wherein the process comprises the steps of:
   a) taking water for injection (WFI) in a manufacturing tank, sparging an inert gas until a dissolved oxygen level is in a range of 0.5 ppm to 2 ppm to produce a solution;
   b) adding maltose and Tigecycline to the solution of step a) in any order and adjusting the pH of the solution between 3-6;

c) optionally filtering the solution obtained in step b) through a suitable filter;
d) filling the solution into vials, and loading the vials into a lyophilizer;
e) lyophilizing the solution in the vials to get the stable lyophilized pharmaceutical composition comprising Tigecycline and maltose.

5. The process for preparation of a stable lyophilized pharmaceutical composition according to claim 4, wherein the maltose is added to the solution of step a) before the addition of the Tigecycline, and wherein hydrochloric acid is added before addition of the Tigecycline.

6. A stable lyophilized pharmaceutical composition prepared by a process according to claim 4, wherein the composition has an impurity of 4-epimer of Tigecycline that is less than 3% throughout a shelf life.

* * * * *